(12) United States Patent
Jabbarzadeh et al.

(10) Patent No.: US 11,471,335 B2
(45) Date of Patent: Oct. 18, 2022

(54) GEL-WITHIN-GEL WOUND DRESSING

(71) Applicant: UNIVERSITY OF SOUTH CAROLINA, Columbia, SC (US)

(72) Inventors: Ehsan Jabbarzadeh, Columbia, SC (US); Sara Eslambolchimoghadam, Columbia, SC (US)

(73) Assignee: University of South Carolina, Columbia, SC (US)

( * ) Notice: Subject to any disclaimer, the term of this patent is extended or adjusted under 35 U.S.C. 154(b) by 500 days.

(21) Appl. No.: 16/539,192

(22) Filed: Aug. 13, 2019

(65) Prior Publication Data

US 2020/0069478 A1 Mar. 5, 2020

Related U.S. Application Data

(60) Provisional application No. 62/727,232, filed on Sep. 5, 2018.

(51) Int. Cl.
| | | |
|---|---|---|
| *A61F 13/00* | (2006.01) | |
| *A61F 13/02* | (2006.01) | |
| *A61L 27/52* | (2006.01) | |
| *A61L 15/42* | (2006.01) | |
| *A61L 15/32* | (2006.01) | |
| *A61L 15/60* | (2006.01) | |

(Continued)

(52) U.S. Cl.
CPC .... *A61F 13/0213* (2013.01); *A61F 13/00068* (2013.01); *A61L 15/425* (2013.01); *A61L 27/52* (2013.01); *A61F 13/0223* (2013.01); *A61F 2013/530802* (2013.01); *A61L 15/28* (2013.01); *A61L 15/325* (2013.01); *A61L 15/60* (2013.01)

(58) Field of Classification Search
CPC ........ A61L 15/60; A61L 15/425; A61L 15/24; A61L 15/32; A61L 15/40; A61L 15/62; A61L 15/42; A61L 2209/133; A61L 2/18; A61L 9/014; A61L 15/20
See application file for complete search history.

(56) References Cited

U.S. PATENT DOCUMENTS

| | | |
|---|---|---|
| 3,972,328 A | 8/1976 | Chen |
| 4,192,785 A | 3/1980 | Chen et al. |

(Continued)

FOREIGN PATENT DOCUMENTS

| | | |
|---|---|---|
| CN | 105412981 | 3/2016 |
| CN | 106492260 | 3/2017 |

(Continued)

OTHER PUBLICATIONS

Armstrong, et al. "Diabetic foot ulcers and their recurrence" *New Eng. J. Med.* 376(24) (2017) pp. 2367-2375.

(Continued)

*Primary Examiner* — Kim M Lewis
(74) *Attorney, Agent, or Firm* — Dority & Manning, P.A.

(57) ABSTRACT

Wound dressings, methods for forming the wound dressings, and methods for using the wound dressings are described. Wound dressings include a crosslinked hydrogel matrix and a plurality of porous absorbent microspheres encapsulated in the crosslinked matrix. The hydrogel matrix and the microspheres can include the same or different hydrogel polymers, e.g., alginates or the like. The wound dressings can be used in treating chronic wounds and burn wounds and can promote autolytic debridement.

18 Claims, 5 Drawing Sheets

(51) Int. Cl.
*A61F 13/53* (2006.01)
*A61L 15/28* (2006.01)

(56) References Cited

U.S. PATENT DOCUMENTS

| | | | |
|---|---|---|---|
| 4,393,080 | A | 7/1983 | Pawelchak et al. |
| 4,538,603 | A | 9/1985 | Pawelchak et al. |
| 4,551,490 | A | 11/1985 | Doyle et al. |
| 4,778,679 | A * | 10/1988 | Silvetti ............... A61K 31/715 424/648 |
| 5,106,629 | A * | 4/1992 | Cartmell ............... A61F 13/023 424/445 |
| 5,181,905 | A | 1/1993 | Flam |
| 5,217,444 | A | 6/1993 | Schoenfeld |
| 5,476,443 | A * | 12/1995 | Cartmell ............... A61F 13/023 206/441 |
| 5,660,790 | A | 8/1997 | Lawrence et al. |
| 5,823,953 | A | 10/1998 | Roskin et al. |
| 5,897,834 | A | 4/1999 | Lawrence et al. |
| 5,910,447 | A | 6/1999 | Lawrence et al. |
| 6,106,461 | A | 8/2000 | Roskin et al. |
| 6,420,623 | B2 | 7/2002 | Augustine et al. |
| 6,570,050 | B2 | 5/2003 | Augustine et al. |
| 7,897,105 | B2 | 3/2011 | Chen |
| 9,855,364 | B2 | 1/2018 | Coomber |
| 2001/0051781 | A1 | 12/2001 | Augustine et al. |
| 2002/0029010 | A1 | 3/2002 | Augustine et al. |
| 2007/0276207 | A1 | 11/2007 | Eagland et al. |
| 2008/0286148 | A1 | 11/2008 | Chen |
| 2009/0190135 | A1 | 7/2009 | Clarizia et al. |
| 2009/0275071 | A1 | 11/2009 | Brusilovsky et al. |
| 2013/0172781 | A1 | 7/2013 | Russo |
| 2014/0236112 | A1 * | 8/2014 | Von Wolff ............... A61L 15/26 604/369 |
| 2015/0308994 | A1 | 10/2015 | Hammond et al. |
| 2016/0106880 | A1 | 4/2016 | Coomber |
| 2018/0093007 | A1 | 4/2018 | Coomber |

FOREIGN PATENT DOCUMENTS

| | | |
|---|---|---|
| DE | 10016383 | 6/2001 |
| DE | 102011082716 | 3/2013 |
| GB | 2353357 | 2/2001 |
| JP | 2018048871 | 3/2018 |
| JP | 2018048872 | 3/2018 |
| KR | 20150033237 | 4/2015 |
| KR | 20160060519 | 5/2016 |
| WO | WO 2012/046087 | 4/2012 |
| WO | WO-2018211458 A1 * | 11/2018 ........... A61B 5/1455 |

OTHER PUBLICATIONS

Bennison, et al. "The pH of wounds during healing and infection: A descriptive literature review" *Wound Pract. Res.: Au. J. Wound Man.* 25(2) (2017) pp. 63-69. (Abstract only).

Bowler, et al. "Wound microbiology and associated approaches to wound management" *Clin. Microbiol. Rev.* 14(2) (2001) pp. 244-269.

Choi, et al. "Intelligent pH indicator film composed of agar/potato starch and anthocyanin extracts from purple sweet potato" *Food Chem.* 218 (2017) pp. 122-128.

Credence Research. "Global Wound Debridement Products Market to Reach Worth US$ 493.1 Mn by 2025" (2018) pp. 1-2.

Dabiri, et al. "Choosing a wound dressing based on common wound characteristics" *Adv. Wound Care* 5(1) (2016) pp. 32-41.

Driver, et al. "The costs of diabetic foot: The economic case for the limb salvage team" *J. Vasc. Surg.* 52(3) (2010) pp. 17S-22S.

Gethin, G. "The significance of surface pH in chronic wounds" *Wounds UK* 3(3) (2007) pp. 52-56.

Golasz, et al. "Film with anthocyanins as an indicator of chilled pork deterioration" *Food Sci. Techn.* 33 (2013) pp. 155-162.

Han, et al. "Chronic wound healing: A review of current management and treatments" *Adv. Ther.* 34(3) (2017) pp. 599-610.

James, et al. "Biofilms in chronic wounds" *Wound Repair Regen.* 16(1) (2008) pp. 37-44.

Jones, et al. "The effect of pH on the extracellular matrix and biofilms" *Adv. Wound Care* 4(7) (2015) pp. 431-439.

Kuhn, et al. "Balancing the pressure ulcer cost and quality equation" *Nurs. Eco.* 10(5) (1992) pp. 353-359. (Abstract only).

Le, et al. "Recent developments in fibres and materials for wound management" *In. J. Fibre Text. Res.* 22 (1997) pp. 337-347.

Liakos, et al. "Controlled antiseptic release by alginate polymer films and beads" *Carbohy. Polym.* 92(1) (2013) pp. 176-183.

Liang, et al. "A pH-Sensing Film from Tamarind Seed Polysaccharide with Litmus Lichen Extract as an Indicator" *Polymers* 10(1):13 (2017) pp. 1-10.

Liu, L. "pH-Indicating Colorimetric Hydrogel for Wound Dressing and Medical Grade Silicone Adhesive for Skin Electronics: Towards Multifunctional Bionic Skin Patch" *U. Alberta* (2016) pp. 1- 103.

MarketsandMarkets. "Wound Care Market worth $22.81 billion by 2022" *Markets and Markets* MD2611 (2017) pp. 1-2. https://www.marketsandmarkets.com/PressReleases/wound-care.asp.

McCallon, et al. "Optimizing wound bed preparation with collagenase enzymatic debridement" *J. Am. Coll. Clin. Wound Spec.* 6(1-2) (2014) pp. 14-23.

Mirani, et al. "An Advanced Multifunctional Hydrogel-Based Dressing for Wound Monitoring and Drug Delivery" *Adv. Healthcare Mater.* 6(19):1700718 (2017) pp. 1-26.

Ono, et al. "Increased wound pH as an indicator of local wound infection in second degree burns" *Burns* 41(4) (2015) pp. 820-824.

Schneider, et al. "Influence of pH on wound-healing: A new perspective for wound-therapy?" *Arch. Dermatol. Res.* 298(9) (2007) pp. 413-420.

Sen, et al. "Human skin wounds: A major and snowballing threat to public health and the economy" *Wound Rep. Regen.* 17(6) (2009) pp. 763-771.

Singer, et al. "Cutaneous wound healing" *New Eng. J. Med.* 341(10) (1999) pp. 738-746.

Sinha, S. "Wound debridement: Doing and teaching" *Prim. Int.: Au. J. Wound Man.* 15(4) (2007) pp. 162-164. (Abstract only).

\* cited by examiner

GEL-WITHIN-GEL WOUND DRESSING

CROSS REFERENCE TO RELATED APPLICATION

This application claims filing benefit of U.S. Provisional Patent Application Ser. No. 62/727,232, having a filing date of Sep. 5, 2018 and entitled "Gel-Within-Gel Dressing for Wound Debridement," which is incorporated herein by reference for all purposes.

FEDERAL RESEARCH STATEMENT

This invention was made with Government support under Grant No. 1811949, awarded by the National Science Foundation, and under Grant No. R03 EB026813, awarded by the National Institutes of Health. The Government has certain rights in the invention.

BACKGROUND

Proper wound care varies with the type of wound. Acute wounds, i.e., wounds due to trauma, surgery, etc., heal through the physiological stages of inflammation, tissue formation, and remodeling, which will naturally occur in a timely fashion if the wound is kept clean. In contrast, chronic wounds such as leg ulcers, foot ulcers, and pressure sores or decubitus ulcers, caused by sustained external skin pressure, do not heal normally and can be detained in or not progress at all through the normal wound healing stages. Chronic wounds require intensive levels of care, and even with intensive treatment, may take years to fully heal or may never heal at all, causing long-term pain, as well as emotional and financial distress to the sufferer. Burn wounds can likewise require intensive long-term treatment and can cause severe pain, distress, and scarring, even with the best of care.

Pathophysiological abnormalities that may predispose an individual to the formation of chronic wounds include compromised tissue perfusion as a consequence of impaired arterial supply (peripheral vascular disease) or impaired venous drainage (venous hypertension) and metabolic abnormalities. Increased incidence of diseases such as diabetes mellitus, aging populations, increasing obesity rates, smoking, poor nutrition, and immunosuppression associated with disease (e.g., AIDS) or drugs (e.g., chemotherapy or radiation therapy) contribute to a rise in the occurrence of chronic wounds and the morbidity associated with them.

It is reported that in the United States, 8 million people have burns or suffer from chronic, non-healing wounds, and it is estimated that 12 million people are currently faced with chronic wounds. The global incidence of diabetic pressure ulcers is estimated to reach 26.1 million people annually. The global burn prevalence is expected to reach 7.1 million injuries. The cost of caring for chronic wounds in the U.S. alone exceeds $50 billion annually, which is 10 times more than the annual budget of the World Health Organization.

An important concept in chronic and burn wound care is the role of debridement: the removal of non-viable tissue material. The goal of debridement is to remove necrotic debris which only serves as fuel for infection and impedes wound healing, and to expose healthy, well-perfused tissue that is able to proliferate and populate the wound bed via epithelial cell migration. There are four different techniques for debridement: Surgical debridement is the quickest and most efficient method of debridement in which a thin layer of slough over the wound bed can be gently removed with the help of a small curette. Unfortunately, this method is associated with bleeding and pain, and it cannot be used for patients with coagulation and blood circulation abnormalities. In mechanical debridement, also known as wet-to-dry dressing, wet saline gauze is allowed to dry on the wound. When the dressing is removed, the dead tissue is simultaneously pulled away. This method is to be avoided as it is very painful and associated with bleeding and damage the delicate granulation tissue. Chemical debridement is performed by using certain enzymes and other compounds to dissolve necrotic tissue but is extremely expensive. In autolytic debridement, the wound is kept very wet with dressings (hydrogels and hydrocolloids in relatively dry wounds; alginates and cellulose in moist wounds) to soften the necrotic tissue, which is removed slowly with repeated dressings.

Wound dressings that maintain a moist wound environment necessary for autolytic debridement to occur include gels, thin films, foams, alginates, and hydrocolloids. Hydrocolloid dressings usually have poor moisture vapor permeability but have some absorptive capability. Hydrogels are similar to hydrocolloids in the ability to absorb and manage wound exudate. Generally, hydrogel dressings do not dissolve into the wound bed as do hydrocolloids. Foam dressings are typically manufactured from synthetic polymeric materials, such as hydrophilic polyurethane, which absorb wound exudate by a sponge-type mechanism. The majority of alginate dressing are fibrous. Alginate fibers are well known and widely used in wound dressing materials in the form of, e.g., knitted alginate (Ultraplast™ styptic gauze wound dressing by Wallace, Cameron & Co. Ltd., Glasgow, Scotland), or a carded web (Steriseal Sorbsan™ surgical dressing by N.I. Medical, Redditch, Worcestershire, England; Kaltostat™ hemostatic wound dressing by Cair Ltd., Aldershot, Hatt, England).

Unfortunately, fibrous alginate wound dressings can be difficult to handle, and because of structural weakness, skill is required to apply the dressings properly, with handling problems aggravated when the dressing or one's fingers are not completely dry. Additionally, because alginate fibers are highly absorbent, dressings based on high-basis weight alginate webs are more likely to desiccate a wound if applied in a dry condition to the wound. Even when fibrous alginate-based wound dressings can be formed to exhibit good integrity when dry, they can become weak and lose integrity when saturated with saline or body fluids. This can cause the dressing to disintegrate while being lifted from a wound, necessitating picking-out or irrigation to remove dressing bits from the wound. Mechanical stability at a swollen state, lack of control over dehydration rate, and skin maceration are major limitations associated with current alginate dressings.

Further progress in development of dressings designed to promote autolytic debridement has included development of thin films, honey-based dressings, and polymeric membrane dressings (PMDs). While providing improvement to the art, such products still exhibit drawbacks. For instance, thin films can exhibit structural issues similar to those of fibrous alginate dressings, and honey-based dressings, such as Medihoney® (a topical autolytic debriding agent with moderate anti-infection and debriding properties), can cause allergic reactions and exhibit low efficacy, as well as long debridement and healing time.

Despite the wide variety of wound dressings available, chronic and burn wounds remain serious medical conditions with limited available dressing options that simultaneously manage the moist wound environment, absorb wound exudates, and leave no residues in the wound bed when the fluid is removed. There is an unmet need in the wound care sector for wound dressings for chronic and burn wounds. Chronic and burn wound dressings that can provide for autolytic debridement would be of particular benefit.

SUMMARY

According to one embodiment, disclosed is a wound dressing that includes a crosslinked absorbent hydrogel matrix that includes a biocompatible polymer. The wound dressing also includes a plurality of porous absorbent microspheres encapsulated in the crosslinked absorbent hydrogel matrix. Each microsphere includes a crosslinked biocompatible polymer, which can be the same or different as the polymer of the hydrogel. Optionally, either or both of the hydrogel matrix and the microspheres can include a plasticizer.

Also disclosed is a method for forming a wound dressing. For instance, a method can include forming a plurality of porous, absorbent microspheres, and distributing the microspheres within a hydrogel precursor. Following this distribution, the hydrogel precursor can be crosslinked, encapsulating the microspheres within the crosslinked absorbent hydrogel matrix.

A method for wound treatment is also disclosed. For instance, a treatment method can include applying a wound dressing as described to a surface of a wound (e.g., a chronic wound or a burn wound), and following a period of time, removing the wound dressing from the surface. Beneficially, the wound dressing at the removal can carry wound exudate, including softened necrotic tissue, and can promote autolytic debridement of the wound.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Figure 1:
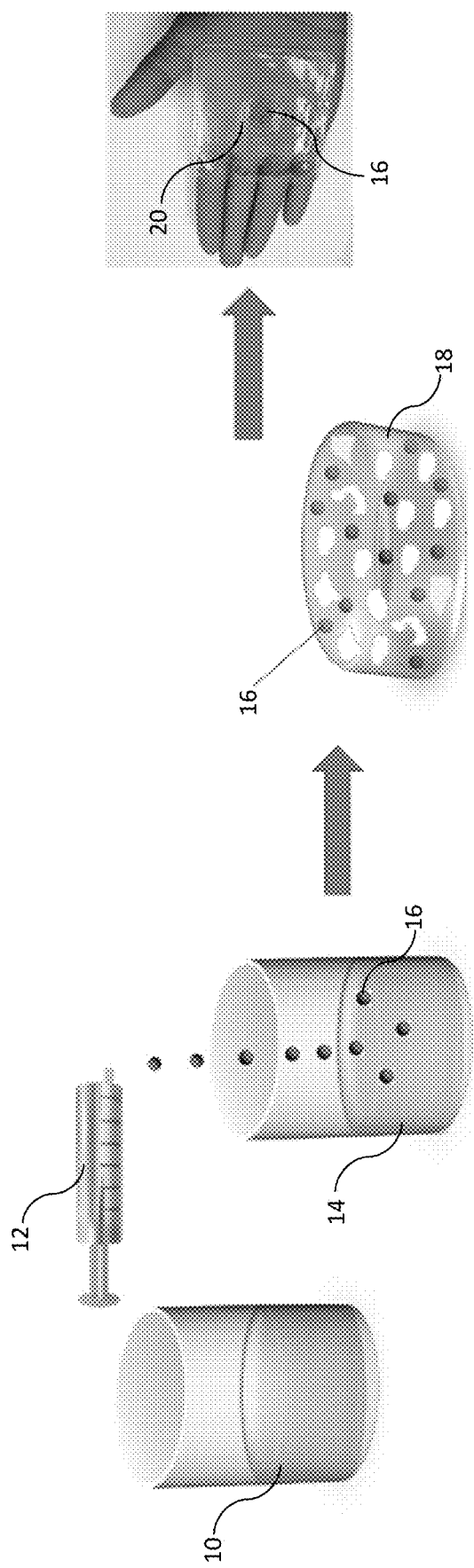
FIG. 1 presents a schematic illustration of a microsphere formation process and a fabrication process for a wound dressing that encapsulates the microspheres within a crosslinked hydrogel matrix.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

The present disclosure is directed to wound dressings. Methods for forming and using the wound dressings are also described. Disclosed wound dressings can promote autolytic debridement and can be particularly beneficial in treating chronic wounds and burn wounds. Disclosed wound dressings can possess a variety of beneficial properties including absorbency without wound desiccation so as to maintain desirable fluid balance at the wound site, ease of application and removal without fear of damage to either the wound area or the wound dressing, and hemostasis and bacterial protection while maintaining gas permeability so as to protect the wound from infection while promoting healing. Moreover, the wound dressings can exhibit mechanical characteristics that accommodate movement while in use without disintegration and do not restrict patient motion.

During use, the disclosed wound dressings can keep wounds moist, which can help promote the natural wound healing process while still protecting the healing wound from infection. The moist occlusive dressings can help support the inflammatory phase of wound healing and can also increase the rate of re-epithelialization during tissue formation and remodeling phases. Moreover, as a limited amount of exudate can be retained on the wound during use of the moist dressings, the dressings can maintain an amount of natural growth factors present in wound exudates that promote healing at the wound site. In addition, the moist dressings can soften necrotic tissue at the wound site while absorbing excess exudate, which can allow for autolytic debridement over repeated use.

The wound dressings include a crosslinked absorptive hydrogel matrix incorporated with porous, absorptive microspheres. The crosslinked hydrogel matrix can maintain moisture so as to eliminate the formation of dry crusty scar tissue and soften necrotic tissue at the wound site. The hydrogel matrix can be absorptive, and as such, can maintain moisture at the wound while also absorbing excess fluids, as well as other undesirable materials exuded from the wound, such as dead leucocytes, epidermal cells, and dermal cells. As the hydrogel matrix can be non-fibrous, problems encountered with previously known fiber-based wound dressings, such as fiber adherence to the wound and separated fibers remaining in the wound, can be avoided. The absorbent hydrogel matrix can also contact a wound with a tensile strength and flexibility that prevents matrix damage while not adhering to the wound.

The hydrogel matrix can be formed from one or more non-toxic, biocompatible polymers that include or can be modified to include crosslinkable functionality. The matrix polymer can include synthetic and/or natural hydrogel-forming polymers. By way of example, and without limitation, hydrogel matrix polymers can include alginates, collagen or derivatives thereof, cellulose or derivatives thereof, poly(lactic-co-glycolic acid) (PLGA) or derivatives thereof, polycaprolactone (PCL) or derivatives thereof, as well as combinations of different polymers, e.g., blends or copolymers thereof.

According to one embodiment, the hydrogel matrix can include an alginate. Alginate is a naturally occurring anionic biocompatible polymer with low toxicity composed of a variety of alginic acids extracted from certain species of seaweeds. Alginate has been extensively investigated for many biomedical applications, including highly absorbent wound dressings. Alginate contains blocks of (1,4)-linked β-D-mannuronate (M) and α-L-guluronate (G) residues. Alginate has strong hydrophilicity and as such, can form a highly absorbent wound dressing. Alginates are commercially available as pads, ropes, or ribbons from a variety of different suppliers. Alginate can be attractive for incorporation in a hydrogel matrix in one embodiment as it is known as an approved material for epidermal applications and has excellent biocompatibility and mechanical properties. Additionally, calcium alginate is known as a natural hemostat that can be removed from a wound site limited or no trauma and discomfort.

The hydrogel matrix polymer is not limited to alginates, however, and other non-toxic, biocompatible hydrogel-forming polymers can be utilized in conjunction with or alternative to an alginate. For instance, in one embodiment, a hydrogel matrix can incorporate collagen, or a derivative thereof, for instance in the form of gelatin. Collagen is one of the main protein components of bone, cartilage, tendons, ligaments, and skin. Gelatin can be obtained from collagen by acidic or basic hydrolysis or thermal degradation of collagen, which leads to rupture of the collagen triple helix into the random coil structure of gelatin.

In one embodiment, the hydrogel matrix can include a cellulose polymer or a derivative of cellulose (e.g., cellulose acetate, sodium carboxymethyl cellulose, ethylcellulose, nitrocellulose, bacterial cellulose, etc.). Cellulose is the most abundant polysaccharide, and it is inexpensive with good processibility, renewability, and ease of physical and chemical modification. It has good mechanical properties, good hydrolytic stability, low toxicity, and excellent biocompatibility.

PCL as may be incorporated in a wound dressing is a hydrophobic, semi-crystalline, resorbable, aliphatic polyester. The crystallinity decreases with increasing molecular weight; and PCL exhibits good solubility and low melting point (59° C.-64° C.), as well as excellent blend-compatibility, making it attractive for application in disclosed wound dressings. PCL can be biodegradable, but the degradation and resorption kinetics of PCL are relatively slow due to its hydrophobicity and high crystallinity, and as such, it can be beneficial in some embodiments as a component of disclosed hydrogels. PCL can be blended or co-polymerized with other polymers, such as PLA or PLGA, in order to modify its physical properties in a desirable fashion.

PLGA is a highly studied biodegradable polymer as may be incorporated in disclosed hydrogel. In vivo, it is hydrolyzed into the non-toxic lactic acid and glycolic acid monomers. PLGA is commercially available in different molecular weights and copolymer compositions. The rate of biodegradation of a PLGA polymer can be controlled through selection of the copolymer ratio and molecular weight.

To form the hydrogel matrix, an aqueous hydrogel precursor solution can be formed that can include the hydrogel matrix polymer and any other desired additives. For instance, a hydrogel precursor solution can be formed that can include from about 0.5% w/v to about 20% w/v of the polymer, for instance from about 1% w/v to about 10% w/v in some embodiments.

In one embodiment, a hydrogel matrix can incorporate a plasticizer, which can improve the mechanical properties and flexibility of the wound dressings. Examples of suitable plasticizers can include, without limitation, dioctylphthalate; castor oil; diacetylated monoglycerides; diethyl phthalate; glycerin; mono- and di-acetylated monoglycerides; polyethylene glycol; propylene glycol; triacetin; triethyl citrate; bis-(2-butoxyethyl) adipate; and bis-(2-ethylhexyl) sebacate polyvinyl alcohol; polyvinyl alcohol; glycerol; and polyethylene glycol. When included, a hydrogel precursor solution can generally include a plasticizer component in an amount of from 0 to about 20 w/v % of the precursor solution.

Additional additives as may be included in a hydrogel precursor solution can include materials as known in the art. For instance, a wound dressing can be used as a vehicle for the sustained release of therapeutic agents, which encompass any agent that can enhance healing by inclusion of the desired therapeutic agent(s) into the hydrogel precursor solutions. Therapeutic agents can include, without limitation, antimicrobial agents, antiseptic agents, anti-inflammatory agents, pain relieving agents, wound closing adhesive agents, etc. Antimicrobial agents may include, for example, sources of oxygen and/or iodine (e.g., hydrogen peroxide or a source thereof and/or an iodide salt such as potassium iodide); antimicrobial metals, metal ions and salts, such as, for example, silver-containing antimicrobial agents (e.g., colloidal silver, silver oxide, silver nitrate, silver thiosulphate, silver sulphadiazine, or any combination thereof); or any combination thereof.

Other examples of additives of a hydrogel precursor solution can include, without limitation, surfactants, electrolytes, pH regulators, colorants, chloride sources, and mixtures thereof. Additives to the hydrogel precursor solution can encompass materials that are retained in the cross-linked hydrogel matrix of the wound dressing, as well as materials that are not retained in the final product. For instance, an additive (e.g., a surfactant) may serve a purpose during formation of the wound dressing and may be removed from the other components following its intended use and during a later stage of formation of the wound dressing.

In some embodiments, a hydrogel precursor solution can include a crosslinking agent and/or a crosslink initiator. In some embodiments, one or both of a crosslinking agent and a crosslink initiator can be added to the hydrogel precursor solution at the time of crosslinking. Conventional biocompatible cross-linking agents as are suitably used to provide the necessary mechanical stability and to control the properties of a hydrogel can be included in a hydrogel precursor solution (or combined with a precursor solution at the time of crosslinking). When included in the hydrogel precursor solution, the amount of crosslinking agent and/or crosslink initiator to be included will be readily apparent to those skilled in the art. For instance, a crosslinking agent can be included in an amount of from about 0.01% w/v to about 0.5% w/v, from about 0.05% w/v to about 0.4% w/v, or from about 0.08% to about 0.3% w/v, of the hydrogel precursor solution. Typical crosslinking agents can include, without limitation, tripropylene glycol diacrylate, ethylene glycol dimethacrylate, triacrylate, and methylene bis acrylamide. In one embodiment, a cationic crosslinking agent can be utilized. For example, a polyvalent elemental cation, such as $Ca^{2+}$, $Mg^{2+}$, $Al^{3+}$, $La^{3+}$, or $Mn^{2+}$, can crosslink polymers of a hydrogel matrix.

When included, a hydrogel precursor solution may include a crosslink initiator in standard amounts, e.g., up to about 5% w/v, for instance from about 0.002% w/v to about 2% w/v. In one embodiment, a hydrogel precursor solution can include a photoinitiator, such as, and without limitation to, benzoyl radicals such as type I-α-hydroxy-ketones and benzilidimethyl-ketals (e.g., Irgacure 651, Irgacure184 and Daracur 1173 as marketed by Ciba Chemicals), as well as combinations thereof.

In some embodiments, crosslinking can be initiated upon contact of a crosslinking agent with the hydrogel precursor solution in conjunction with suitable crosslink initiation parameters as necessary (e.g., temperature or light). For instance, a hydrogel precursor solution containing sodium alginate as the hydrogel polymer can be combined with a divalent cation (via e.g., a $CaCl_2$) solution) and crosslinking can spontaneously occur via ion exchange.

The wound dressing includes a plurality of porous, absorptive microspheres encapsulated in the crosslinked hydrogel matrix. The porous absorptive microspheres include a crosslinked polymer and can be formed of a crosslinked hydrogel polymer that can be the same or different hydrogel polymer as used in the crosslinked hydrogel matrix. For instance, the porous absorptive microspheres can include one or more non-toxic, biocompatible polymers that include or can be modified to include crosslinkable functionality. The microsphere polymer can include synthetic and/or natural hydrogel-forming polymers. By way of example, and without limitation, microsphere polymers can include alginates, collagen or derivatives thereof, cellulose or derivatives thereof, poly(lactic-co-glycolic acid) (PLGA) or derivatives thereof, polycaprolactone (PCL) or derivatives thereof, polycaprolactone (PCL) or derivatives thereof, as well as combinations of different polymers (e.g., blends or copolymers thereof), as discussed previously.

The porous absorptive microspheres can include one or more additives, including additives as discussed previously with regard to the hydrogel precursor solution such as, and without limitation to, plasticizers, therapeutic agents, surfactants, electrolytes, pH regulators, colorants, chloride sources, and mixtures thereof.

A microsphere precursor solution can include the various components in amounts as described above with regard to the hydrogel precursor solution. In one embodiment, the microsphere precursor solution can be the same as the hydrogel precursor solution (i.e., the same additives in the same proportions). In another embodiment, the precursor solutions can differ. By way of example, the hydrogel precursor solution and the microsphere precursor solution can be based upon the same crosslinkable polymer (e.g., an alginate), and the solutions can differ from one another by the inclusion of a therapeutic agent or a plasticizer or by the add-in amount of an additive. Of course, the hydrogel precursor solution and the microsphere precursor solution can differ with regard to inclusion or amount of any components, including the biocompatible crosslinkable polymer upon which the solution is based.

The porous, absorptive microspheres can be formed according to any suitable formation method including, without limitation, ultrasonic methods, mechanical methods (e.g., high energy stirring), emulsification condensation, spray condensation, etc. In one embodiment, the formation technique and/or particular characteristics of the formation technique can be designed to control the size of the microspheres. In general, however, the microspheres can be formed to any size in the micrometer scale, e.g., from about 1 micrometer to about 1 millimeter.

Modification of the size of the microspheres in conjunction with the concentration of the microspheres in the crosslinked hydrogel matrix can be utilized to control characteristics of the wound dressing including, without limitation, wicking effects including movement of fluid into the dressing, which creates osmotic pressure leading to wound debridement. In addition, variation of microsphere size and concentration can allow for tuning of the mechanical properties (e.g., stretchability and stiffness modulus) of the wound dressing, as well as tuning of the rate of dehydration and the degree of swelling. Depending on the desired application and formulation characteristics, different parameters can be modified to produce a gel or matrix for wound repair having designed characteristics within narrow specifications.

By way of example, FIG. 1 schematically illustrates one method for formation of the porous, absorptive microspheres and encapsulation of the microspheres into a crosslinked hydrogel matrix. As illustrated, following formation of a microsphere precursor solution 10, an injector 12 can inject nascent spheres of the microsphere precursor solution 10 into an agitated bath 14 that includes a crosslinking agent and/or a crosslink initiator under conditions to initiate crosslinking of the microsphere precursor solution to form the porous absorbent microspheres 16.

The porous absorbent microspheres 16 can then be distributed within a hydrogel precursor solution 18. The distribution can be carried out according to any methodology. For instance, the hydrogel precursor solution can be simply mixed with the microspheres prior to crosslinking. In one embodiment, the hydrogel precursor solution can be partially solidified, so as to prevent agglomeration of the microspheres prior to final crosslinking of the solution. By way of example, a hydrogel precursor solution can be located in a mold or cast in a desired shape (e.g., a thin film), and then dehydrated to remove at least a portion of the water of the precursor solution and solidify the precursor. Following solidification, the microspheres can be dispersed as desired on or in the precursor Following combination of the porous absorbent microspheres and the hydrogel precursor solution (or a solidified hydrogel precursor), the hydrogel precursor solution 18 can be crosslinked by, e.g., addition of a crosslinking agent to the system, addition of a crosslink initiator to a system, addition of crosslinking conditions to a system, or any combination thereof. Upon crosslinking, the crosslinked absorbent hydrogel matrix 20 can encapsulate a plurality of the porous absorbent microspheres 16 distributed therein.

Encapsulation of the porous, absorbent microspheres into the crosslinked hydrogel matrix can provide multiple benefits to the wound dressing, including reduction of Young's modulus and increase of elasticity as compared to a crosslinked hydrogel matrix formed without inclusion of the microspheres. For instance, a crosslinked hydrogel matrix encapsulating a plurality of porous absorbent microspheres as described can exhibit a Young's modulus of about 1 mPa or less, or about 0.5 mPa or less, in some embodiments.

Incorporation of a plurality of the porous absorbent microspheres can also reduce dehydration rate of a wound dressing compared to a similar wound dressing without microspheres. As such, the wound dressing can remain moist at the wound site for a longer period of time as compared to moist wound dressings that exhibit fast drying rates, and as such must be replaced more often in order to retain desired moisture and promote autolytic debridement.

Encapsulation of the microspheres within the crosslinked hydrogel matrix prevents the microspheres from dispersing into the wound area while providing a biocompatible interface with the wound site to improve characteristics of the wound dressing. During use, once the wound dressing is in contact with tissue fluid, e.g., exudate, the wound dressing can swell and soften (or dissolve, depending upon the particular characteristics of the crosslinked polymers) at a predetermined rate to form a viscous gel. In one embodiment, the polymer of the porous microspheres (e.g., a collagen, an alginate or another biocompatible polymer) can be selected so as to modify and control the rate of water vapor transmission from the wound surface, water absorbance, dehydration, and mechanical properties of the wound dressing as compared to a similar dressing that is formed without the encapsulated microspheres.

Wound dressings as described can be utilized in treating any moist wound, and in particular chronic wounds, but are not limited to such uses, and the wound dressings can be effective against many other forms of wounds and skin disease. For example, disclosed wound dressings can be effective for use as general surgical wound dressing, burn dressing, donor site dressing, bedsore dressing, and ulcer dressing and like applications, as well as in skin care-medical (dermatology) or cosmetic applications. The wound dressings are suitable for partial- and full-thickness wounds with moderate to heavy exudate and due to their ability to retain moisture, may not require dressing changes as frequently as other, previously known wound dressings.

Exemplary wound problems that can utilized the wound dressings can include, without limitation, ulcers, sunburns, traumatic injuries, hemorrhoids, bedsores, diabetic wounds, and ischemic syndromes such as coronary or peripheral arterial disease and angiogenesis-dependent disease. Moreover, the wound dressings can be used as the primary wound treatment protocol or in combination with other products and debridement techniques such as surgical debridement.

In one embodiment, the wound dressings can be utilized for autolytic debridement. According to this embodiment, a wound dressing can be placed over a wound and can keep the wound moist while absorbing a portion of the wound exudate. However, a portion of the wound exudate can remain, which can allow the endogenous enzymes within the wound fluid to digest and liquefy necrotic tissue. The wound dressing can typically be left in place for 2-3 days. Upon removal, the absorbent wound dressing can carry the absorbed exudate away from the wound. The wound can then be irrigated with normal saline to remove additional liquefied debris prior to placement of a fresh wound dressing on the wound.

Disclosed wound dressings offer a broad range of advanced healing modalities and can be used in treating multiple different types of wounds. Moreover, the design approach is versatile and can be formulated as a topical gel or in the form of a pre-formed film.

The present disclosure may be better understood with reference to the Examples set forth below.

EXAMPLE

Preparation of Alginate Microspheres

A solution of sodium alginate/glycerol (2% w/v-10% w/v) (Sigma-Aldrich-Fisher Scientific) in DI water was prepared and homogenized at 800 rpm using stirrer for 1 hour. Homogenized solution was put into a sonication bath to remove the trapped air bubbles. Alginate solutions was loaded into a syringe and ejected from a 25-gauge needle into agitated bath of 200 mL of CaCl2 (2% w/v). (Sigma-Aldrich) as cross linker. The calcium-cross-linked alginate beads kept in the curing bath for 20 minutes, subsequently filtered and rinsed with DI water to remove excess CaCl2).

Fabrication of the Hydrogel Precursor Base

An alginate precursor base was prepared by casting-solvent evaporation technique. Sodium alginate (2% w/v) in DI water was mixed with different concentration of glycerol (0%-20%), homogenized at 800 rpm using stirrer for 1 hour. Homogenized precursor solution was put into a sonication bath to remove the trapped air bubbles. Different precursor solutions of alginate/glycerol were prepared and cast on a petri dish or a mold followed by oven-drying at 40 C.° for 4 h to make a solid gel precursor base.

Fabrication of the Wound Dressing

Alginate microspheres were added at the concentrations of 50,100, and 200 mg as a second layer to an alginate/glycerol solidified precursor base (2%-10%) followed by addition of more of the alginate/glycerol precursor solution; the resulting structure was oven-dried overnight. To cross-link and form a wound dressing, an aqueous solution of $CaCl_2$) (2% w/v) was poured into the mold or petri dish and left at room temperature for 20 minutes to solidify. Cross-linked sheets were removed and immersed in DI water for 5 minutes to remove excess $CaCl_2$). Glycerol was added to alginate to reduce the dehydration of the wound dressings. Moreover, dressings that were made from glycerol maintained their mechanical integrity and flexibility after complete dehydration and improved the stretchability of the dressing.

The fabricated dressing impregnated with microspheres is flexible and can create conformal contact with skin. The suggested technique is scalable and can be used to fabricate hydrogel based wound dressing with a wide range of sizes and material. Encapsulation of the beads within the hydrogel prevented the beads from dispersing in the wound area.

Dehydration and Hydration Test

To assess the weight loss of different compositions, wound dressings were prepared in circular petri dishes. Following the gel formation, samples were kept at ambient room temperature, and weight was measured during time intervals of 24 hours. Dehydration rate was calculated for three samples of each condition.

Figure 2:
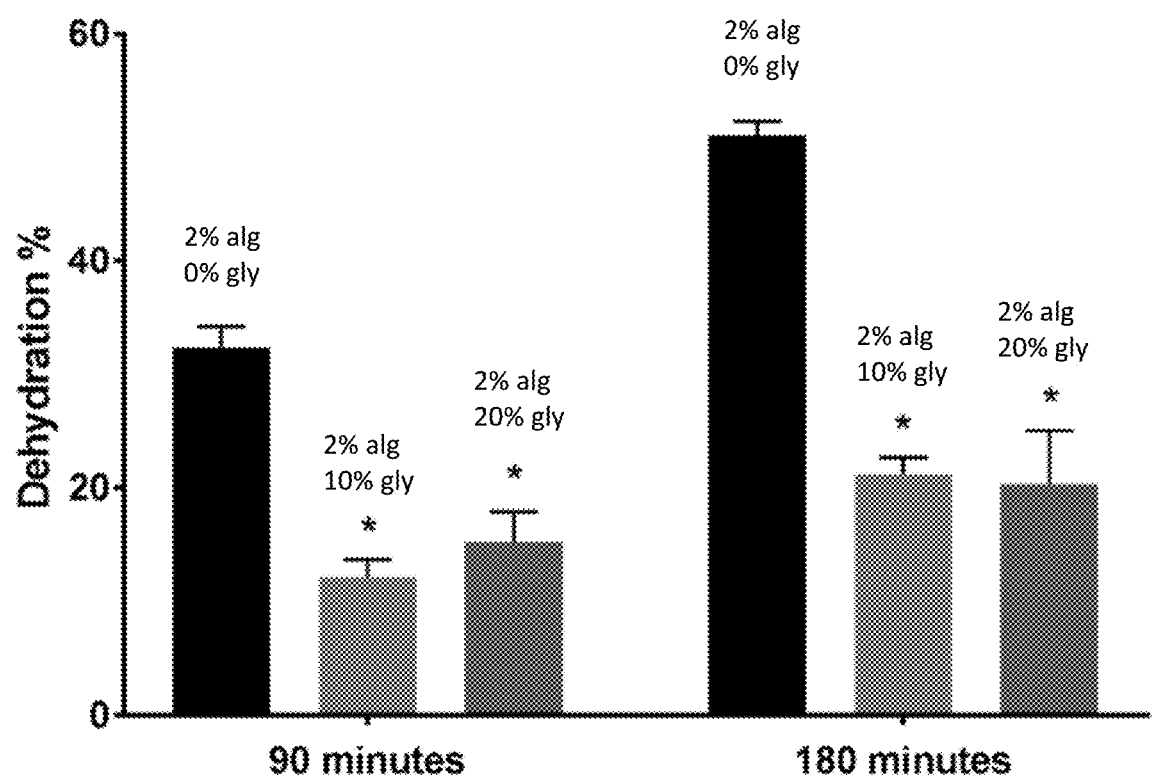
FIG. 2 presents dehydration rate of alginate compositions including different concentrations of glycerol. * denotes significance ($p \leq 0.05$) as compared to the control (2% alginate without glycerol).

FIG. 2 demonstrates dehydration rates of the wound dressings formed with different concentrations of glycerol. As shown, addition of glycerol to the alginate reduced dehydration rate of the dressing significantly. The dehydration rate of the wound dressings was evaluated by measuring the weight loss. Observations indicated that the dressings with glycerol had 20% dehydration in 180 minutes compared to alginate dressings alone demonstrating 50% dehydration. Addition of glycerol to alginate reduced dehydration rate of dressing significantly.

Figure 3:
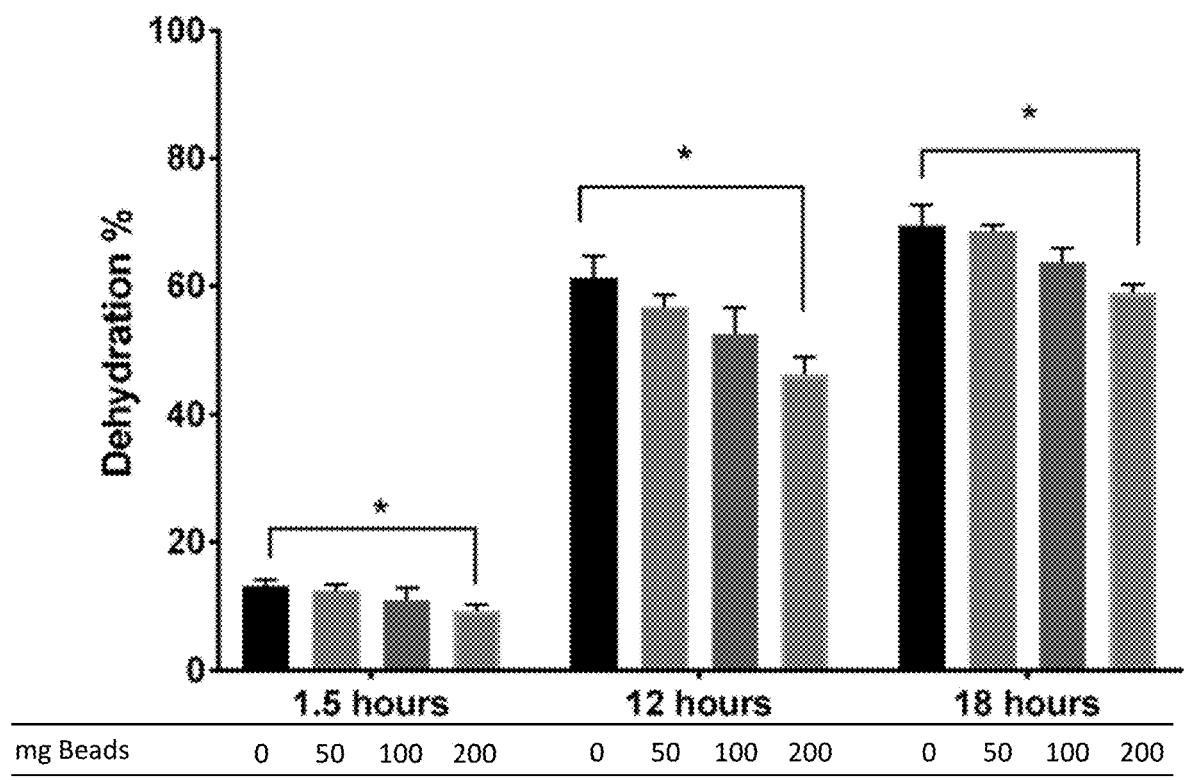
FIG. 3 presents dehydration rate of alginate hydrogels including different concentrations of alginate microspheres. * denotes significance ($p \leq 0.05$) between the two compared groups.

FIG. 3 demonstrates dehydration rate of the wound dressings formed with different concentrations of alginate microspheres. As shown, the dehydration rate was slower when a wound dressing was incorporated with microspheres.

For the hydration test, dried wound dressings at room temperature were immersed in phosphate buffered saline (PBS, pH 7.4). At specific time intervals samples were weighed and all measurement was conducted for three samples.

Figure 4:
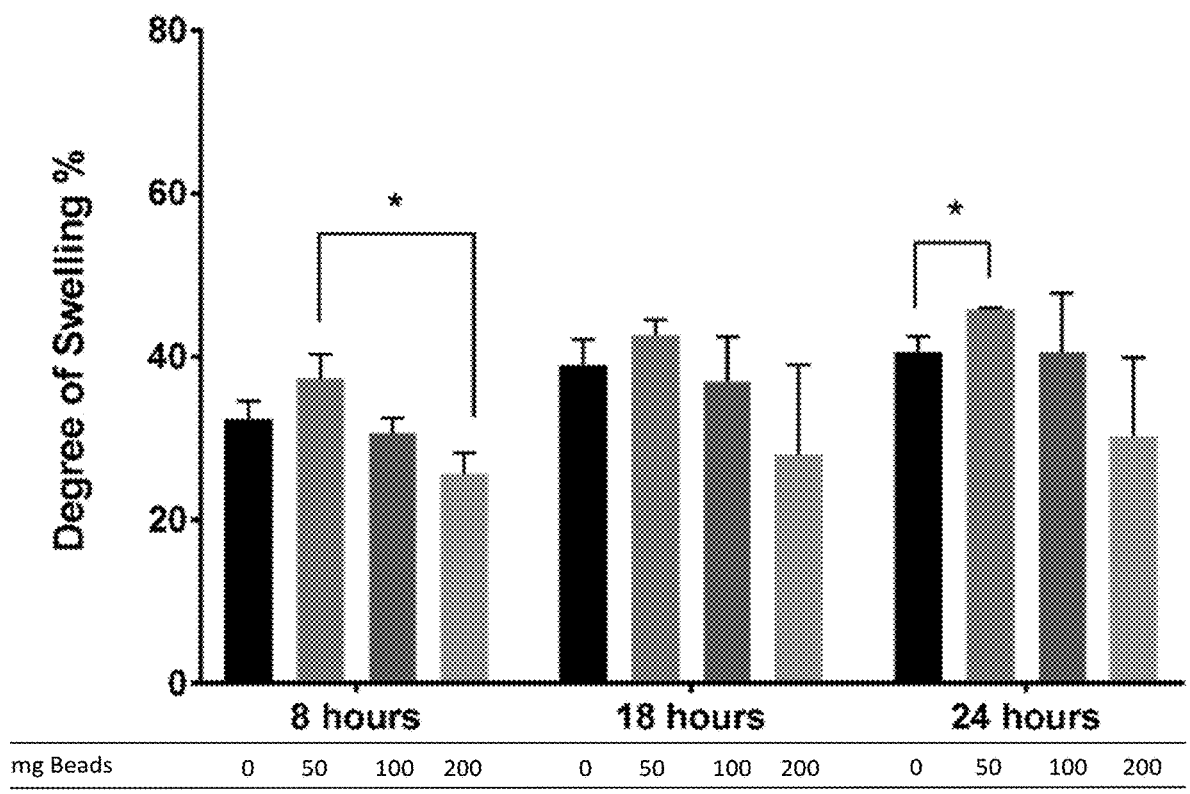
FIG. 4 presents degree of swelling of wound dressings including different concentrations of alginate microspheres. * denotes significance ($p \leq 0.05$) between the two compared groups.

FIG. 4 demonstrates the degree of swelling of wound dressings including different concentrations of microspheres. As shown, the swelling in PBS at 24 hours was higher for the wound dressings incorporating 50 mg of microspheres, as compared to control.

Mechanical Testing

To test the mechanical characteristics of the wound dressing, dressings with different concentrations of beads were cut into strips with dimension of 10 cm×4 cm. Each end of a sample was gripped and stretched at a speed of 100 mm/min. The Young's modulus (E) was measured from the slope of the linear section of the stress-strain curve.

Figure 5:
FIG. 5 presents Young's modulus of wound dressings including different concentrations of alginate microspheres. * denotes significance ($p \leq 0.05$) between the two compared groups.

FIG. 5 demonstrates the effect of microspheres concentrations in wound dressings on the mechanical integrity and flexibility. As shown, addition of the microspheres led to a reduction of Young's modulus in a dressing and improved the stretchability of the dressing as compared to the control, which did not include microspheres. Addition of alginate microspheres led to the reduction of Young's modulus which was significant for groups containing 100 and 200 mg of microspheres.

While certain embodiments of the disclosed subject matter have been described using specific terms, such description is for illustrative purposes only, and it is to be understood that changes and variations may be made without departing from the spirit or scope of the subject matter.

What is claimed is:

1. A wound dressing comprising:
a crosslinked absorbent hydrogel matrix comprising a first biocompatible polymer;
a plurality of porous absorbent microspheres encapsulated in the crosslinked absorbent hydrogel matrix, each porous absorbent microsphere comprising a crosslinked second biocompatible polymer, wherein the first biocompatible polymer and the second biocompatible polymer are the same.

2. The wound dressing of claim 1, wherein the crosslinked absorbent hydrogel matrix and/or the porous absorbent microspheres further comprise a plasticizer.

3. The wound dressing of claim 2, wherein the plasticizer comprises dioctylphthalate, castor oil, diacetylated monoglycerides, diethyl phthalate, glycerin, mono- and di-acetylated monoglycerides, polyethylene glycol, propylene glycol, triacetin, triethyl citrate, bis-(2-butoxyethyl) adipate, and bis-(2-ethylhexyl) sebacate polyvinyl alcohol, polyvinyl alcohol, glycerol, or polyethylene glycol.

4. The wound dressing of claim 1, wherein the first biocompatible polymer and the second biocompatible polymer are selected from an alginate, a collagen, a gelatin, a cellulose, a poly(lactic-co-glycolic acid), a polycaprolactone, or derivatives or combinations thereof.

5. The wound dressing of claim 1, wherein the crosslinked absorbent hydrogel matrix and/or the porous absorbent microspheres further comprise a therapeutic agent.

6. The wound dressing of claim 1, wherein the crosslinked absorbent hydrogel matrix and/or the porous absorbent microspheres further comprise a surfactant, an electrolyte, a pH regulator, a colorant, a chloride source, or a combination thereof.

7. A method for forming a wound dressing comprising:
forming a plurality of porous absorbent microspheres, the porous absorbent microspheres comprising a crosslinked first biocompatible polymer;
forming a hydrogel precursor according to a method that includes forming a hydrogel precursor solution and removing water from the hydrogel precursor solution to form a hydrogel precursor base; and
distributing the plurality of porous absorbent microspheres within the hydrogel precursor; and
crosslinking the hydrogel precursor.

8. The method of claim 7, wherein the method for distributing the plurality of porous absorbent microspheres within the hydrogel precursor comprises distributing the plurality of porous absorbent microspheres across a surface of the hydrogel precursor base, coving the porous absorbent microspheres with additional hydrogel precursor solution, and removing water from the additional hydrogel precursor solution.

9. The method of claim 7, wherein the hydrogel precursor solution comprises from about 0.5% w/v to about 20% w/v of a second biocompatible polymer.

10. The method of claim 7, wherein the hydrogel precursor solution comprises from 0 to about 20w/v % of a plasticizer.

11. The method of claim 7, wherein the plurality of porous absorbent microspheres has been formed according to a method that includes injecting a microsphere precursor solution into a solution that includes a crosslinking agent and/or a crosslink initiator.

12. The method of claim 7, wherein the hydrogel precursor is crosslinked through contact of the hydrogel precursor with a crosslinking agent or a crosslink initiator.

13. A method for treating a wound comprising:
applying a wound dressing to the wound, the wound dressing comprising a crosslinked absorbent hydrogel matrix comprising a first biocompatible polymer and a plurality of porous absorbent microspheres encapsulated in the crosslinked absorbent hydrogel matrix, each porous absorbent microsphere comprising a crosslinked second biocompatible polymer, wherein the first biocompatible polymer and the second biocompatible polymer are the same;
maintaining moisture at the wound with the wound dressing; and
following a period of time, removing the wound dressing from the wound, the wound dressing at removal carrying exudate from the wound.

14. The method of claim 13, wherein the wound is a chronic wound.

15. The method of claim 13, wherein the wound is a burn wound.

16. The method of claim 13, wherein the method further comprises irrigating the wound, the irrigation removing debris from the wound.

17. The method of claim 16, wherein the debris comprises liquefied necrotic tissue.

18. The method of claim 17, wherein the method further comprises applying a fresh wound dressing to the wound and repeating the method for autolytic debridement of the wound.

* * * * *